United States Patent [19]
Parins et al.

[11] Patent Number: 5,125,928
[45] Date of Patent: Jun. 30, 1992

[54] ABLATION CATHETER WITH SELECTIVELY DEPLOYABLE ELECTRODES

[75] Inventors: David J. Parins, White Bear Lake; Mark A. Rydell, Golden Valley; Peter Stasz, Moundsview, all of Minn.

[73] Assignee: Everest Medical Corporation, Minneapolis, Minn.

[21] Appl. No.: 656,799

[22] Filed: Feb. 19, 1991

Related U.S. Application Data

[62] Division of Ser. No. 580,782, Sep. 10, 1990, which is a division of Ser. No. 337,426, Apr. 13, 1989, Pat. No. 4,976,711.

[51] Int. Cl.⁵ .............................. A61B 17/39
[52] U.S. Cl. ................................. 606/48
[58] Field of Search ........... 606/33, 41, 45, 46, 606/48, 50; 128/786

[56] References Cited

U.S. PATENT DOCUMENTS
4,776,349 10/1988 Nashef .................. 128/786

FOREIGN PATENT DOCUMENTS
3516830 11/1986 Fed. Rep. of Germany ...... 128/786
2310775 12/1976 France .................. 128/786

Primary Examiner—Lee S. Cohen
Attorney, Agent, or Firm—Haugen and Nikolai

[57] ABSTRACT

A RF ablation catheter for removing athero-stenotic lesions or modifying the tissue characteristics of the interior walls of selected blood vessels is described. The catheter is characterized in having a tip member which during the initial placement of the catheter within the vascular system so that the distal tip member is disposed in a working relation with the lesion to be removed, means are provided for increasing the cross-sectional profile of the tip members to thereby cause it to move into engagement with the lesion to be excised. The application of an RF voltage across a pair of bipolar electrodes is used to create an electric arc for effecting the cutting action, or alternatively, just sufficient RF energy to sear or otherwise alter the tissue surfaces engaged by the distal tip member.

5 Claims, 3 Drawing Sheets

ABLATION CATHETER WITH SELECTIVELY DEPLOYABLE ELECTRODES

This is a Divisional of copending prior U.S. application Ser. No. 07/580,782, filed on Sep. 10, 1990, which is divisional U.S. application of prior application Ser. No. 07/337,426, filed Apr. 13, 1989, now U.S. Pat. No. 4,976,711.

BACKGROUND OF THE INVENTION

I. Field of the Invention

This invention relates to electrosurgical apparatus and more specifically to bipolar electrosurgical devices for use in intravascular surgery for ablating stenotic deposits adhering to the inner walls of the blood vessel.

II. The use of radio frequency powered instruments for cutting tissue and/or coagulating blood at a bleeding site is well known in the art. For example, reference is made to the Herczog et al U.S. Pat. No. 4,248,231 describing a scalpel having a blade in the form of an insulating substrate on which closely spaced conductive electrodes are affixed. When radio frequency energy of a sufficient potential is applied between the electrodes and the blade is made to cut into tissue, a current flow develops through the tissue bridging the two electrodes resulting in coagulation. In the Stasz U.S. Pat. No. 4,674,498, and entitled "ELECTRO-CAUTERY SURGICAL BLADE", there is disclosed a scalpel arrangement in which the blade also has conductive traces thereon and which are insulated from one another forming a bipolar electrode pair. When RF energy of a predetermined level is applied across the electrodes and the scalpel blade is brought near to the tissue, cutting occurs due to the creation of a arc discharge which creates such high heat energy that the cells comprising the tissue adjacent the instrument desiccate and are severed.

In treating calcified tissue deposits, an rf spark discharge has been used to create a shock wave which, when coupled through a fluid medium to the tissue deposit, results in a breakup thereof (lithotripsy).

II. Discussion of the Prior Art

The buildup of atheromas or the formation of thrombi in a blood vessel can cause serious circulatory problems and when complete blockage occurs, distal tissues may be deprived of oxygen and nutrients, leading to damage or destruction of cell tissue distally of the blockage. As the blockage grows, distal tissue may become more ischemic unless, of course, channelization occurs whereby blood bypasses the constriction. With a narrowed blood vessel, a point may be reached where even a tiny thrombus becomes lodged creating an infarct.

The treatment of diseased blood vessels depends to a large extent on the location of the blockage. In the case of a blocked or partially blocked coronary artery, it has been the practice to perform coronary bypass surgery. In a like fashion, blood vessel shunts have been installed in other body areas as well. The surgery involved in those procedures tends to be quite traumatic, involving, in the case of coronary-bypass surgery, the opening of the patient's chest and pericardium. In treating deep vein thrombosis or other blockages in the peripheral vasculature, extensive excision and vessel replacement is often required.

More recently, following the technique credited to A. Grunzig, a balloon catheter has been used to restore patency to blood vessels without extensive surgery. In carrying out this technique, a catheter having a small inflatable balloon on its distal end is routed through the vascular system to the site of the restriction to be treated. The deflated balloon is appropriately positioned to span the blockage in question and then a fluid is introduced into the proximal end of the catheter to inflate the balloon to a sufficiently high pressure whereby the blockage is spread open and patency is restored.

As is pointed out in U.S. Pat. No. 4,445,509 to Auth, there are some deficiencies in the Grunzig procedure which renders it ineffective in certain applications. For example, the blockage may be such that it is not possible to safely force the distal tip of the catheter through the blockage prior to the inflation of the balloon. The Auth patent also cites a number of other U.S. patents relating to catheter-mounted cutting devices intended to "tunnel" through a blockage but without doing damage to the healthy blood vessel tissue The invention of the Auth patent is in the design of a rotatably driven cutting tool which will preferentially abrade hard or calcified lesions while not significantly abrading the endothelial lining of the blood vessel.

SUMMARY OF THE INVENTION

In accordance with the present invention, there is provided an RF ablation catheter especially designed for removing stenotic lesions from seriously blocked blood vessels. The device comprises an elongated, plastic, flexible, tubular member which is dimensioned so as to pass through a guide catheter to the site of the lesion to be treated. Disposed on the distal end of the catheter body is a tip member which includes first and second spaced electrodes, with the tip member being configured to present a relatively low profile as the catheter is being advanced through the vascular system to the site of the lesion but then expandable to an increased cross-sectional profile such that the electrodes will be brought into touching relation relative to the stenotic lesion to be ablated. By operating at sub-burning temperatures, it is also possible to use the implement to modify the cell structure of the vessel wall as by searing.

In accordance with a first embodiment, the enlargement is achieved through the inflation of a balloon-like expander member forming a part of the tip member. In a first alternative arrangement, the bipolar electrodes are formed on an umbrella-like member which, when collapsed may reside within the lumen of a tubular guide catheter. When the umbrella-like tip member is displaced distally relative to the catheter body, it opens up to present the electrode pair to the lesion to be removed.

In still another arrangement, the first and second electrodes are wrapped as coils around an insulating frame comprising plural thin flat strips which are secured at one end to the tubular member and whose other ends are secured to a further tube or wire running through the lumen of the first tubular member. When the inner tube is extended out from the distal end of the outer tubular member, the turns of the coils lie in planes which are inclined at a relatively small acute angle relative to the longitudinal axis of the catheter assembly When the inner tubular member is drawn in the proximal direction while the outer tubular member is held fixed, the thin flexible strips bow outward, causing the electrode coils to stand up in a more perpendicular relationship relative to the longitudinal axis of the catheter.

In yet another embodiment, the electrodes themselves form a plurality of strips bonded at one end to the exterior surface of the outer tubular member and to the outer surface of a coaxially positioned inner tubular member. Again, by drawing back on the inner tubular member, the conductive electrode strips are made to bow outwardly, increasing the cross-sectional profile of the catheter's tip member.

In still another embodiment, the tip member includes a rotatable segment which, by manipulation of a guide wire extending through the lumen of the tubular member, can be made to rotate out of coaxial alignment with the catheter body to expose a pair of bipolar electrodes formed on the rotatable segment.

DESCRIPTION OF THE DRAWINGS

The foregoing features and advantages of the invention will become apparent to those skilled in the art from the following detailed description of several embodiments of the present invention in which like numerals in the several views refer to corresponding parts.

DESCRIPTION OF THE PREFERRED EMBODIMENT

Figure 1:
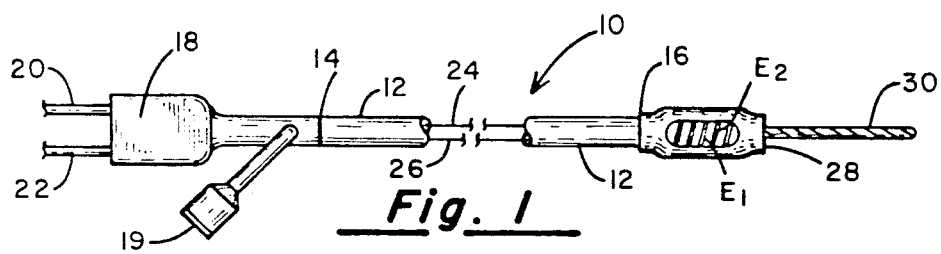
FIG. 1 is a side elevational view of an intravascular catheter.

Referring first to FIG. 1, there is depicted a side elevational view showing the general configuration of an RF intravascular ablation catheter. It is seen to include an elongated, flexible plastic tubular member 12 having a proximal end 14 and a distal end 16. Affixed to the proximal end 14 of the catheter body 12 is an electrical connector 18 having first and second terminal pins 20 and 22 which are adapted to be plugged into the output jacks of a suitable RF voltage generator (not shown). A fluid port 19 communicating with the lumen of tube 12 is integrally molded with the connector 18 and includes a Luer fitting to facilitate its coupling to either a fluid source or to a vacuum. A pair of electrical wires 24 and 26 run the entire length of the catheter body 12 and are joined at the distal end to bipolar electrodes $E_1$ and $E_2$ disposed on a tip member 28. The intravascular RF ablation catheter may also include a fixed guidewire 30 attached to the distal end of the tip member 28. It is found that such a fixed guidewire greatly facilitates the threading of the catheter through the vascular system to a designed treatment site.

The tubular body member 12 can be fabricated from a variety of medical grade plastics including silicon rubber, polyethylene, polyurethane, or other polyesters. The tip member 28 is preferably formed from a suitable ceramic capable of withstanding the temperatures encountered during the course of an ablation procedure. Silicon nitride and aluminum nitride are preferred. Similarly, the electrodes $E_1$ and $E_2$ may be formed from platinum, tungsten or other conductive metal capable of being exposed to an arc discharge without significant deterioration.

As will be explained in greater detail hereinbelow, an important aspect of the ablation catheter of the present invention is that as the catheter is being routed through the vascular system, its tip member exhibits a low cross-sectional profile. Upon reaching the site in the blood vessel where ablation of a stenotic lesion is to take place, means are provided in the tip member for effectively increasing its cross-sectional profile and thus bringing the electrodes $E_1$ and $E_2$ into engagement with the tissue to be excised.

Figures 2, 3:
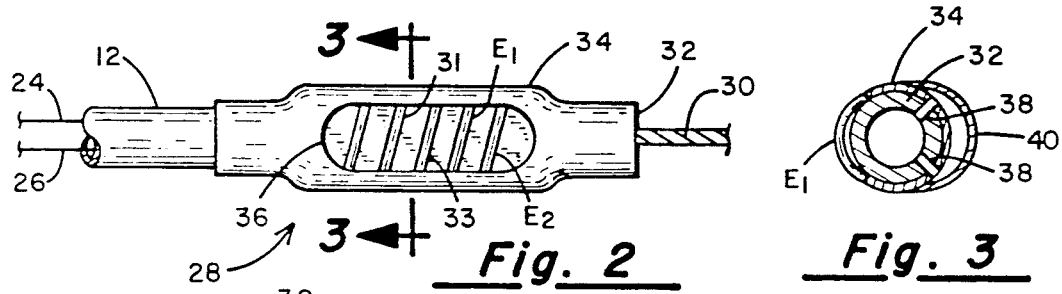
FIG. 2 is an enlarged view of the distal tip portion of the catheter of FIG. 1 in accordance with a first embodiment of the invention.
FIG. 3 is a cross-sectional view of the tip member of FIG. 2 taken along the line 3—3.

Referring next to FIG. 2, there is shown one type of tip member 28 embodying the foregoing features of the present invention. It is seen to include a tubular segment 32 on which is wound first and second helical coils 31 and 33 with the turns being interlaced with one another. The turns are conveniently held in place on the ceramic core by virtue of a coating of a Teflon ® plastic layer 34. Teflon ® has been found to be well suited to this particular application because it is a high temperature plastic/elastomer capable of withstanding the range of temperatures through which the electrodes must undergo. Besides Teflon ®, a ceramic epoxy can be used to bond the electrode coils to the ceramic base. Layer 34 covers a majority of the surface of the conductive windings 31 and 33, except that during the coating process, the assembly is masked to create a window 36 through which the bare metal of the turns is exposed to form electrode surfaces $E_1$ and $E_2$. The conductor 24 passing from the proximal connector pin 20 and through the lumen of the tub 12 is connected at its distal end to the helical conductor on which electrode $E_1$ is exposed and, likewise, the conductor 26 connected to pin 22 at its proximal end is connected to the winding on which the electrode surface $E_2$ is exposed (through the window 36).

Figure 4:
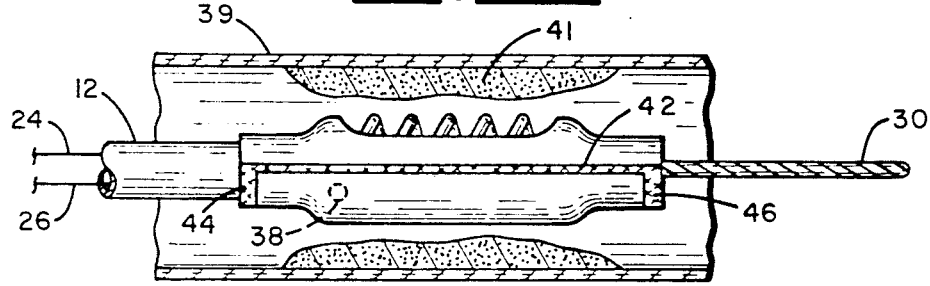
FIG. 4 illustrates the tip member of FIG. 2 in its low profile condition juxtaposed with a stenotic lesion to be treated.
Figure 5:
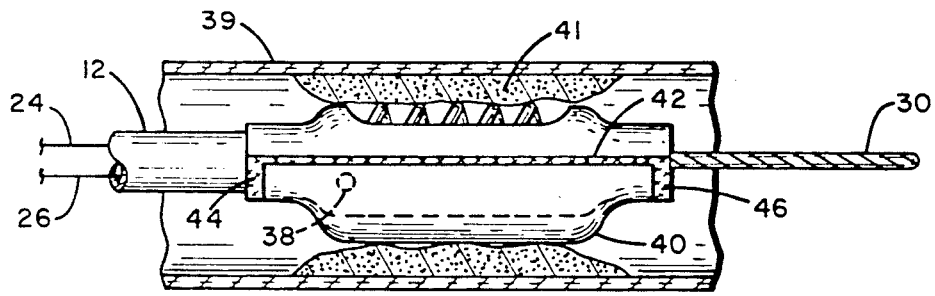
FIG. 5 is a view of the tip member in its large profile condition.

Hidden from view in FIG. 2 but visible in the cross-sectional view of FIG. 3 are fluid ports 38 extending through the wall of the ceramic tubular substrate 32 and the covering of plastic 34 coated thereon. A thin plastic membrane 40 attached to the underside of the tip member is bonded longitudinally to the plastic coating 34 along a seam line 42 and transversely about the proximal and distal ends of the ceramic member 32 as identified by numerals 44 and 46 in FIGS. 4 and 5. Thus, the membrane 40 is sealed along all of its edges and surrounds the undersurface of the tip member as best illustrated in FIGS. 4 and 5 forming an inflatable expander. It is also to be noted that the fluid ports 38 lie beneath the membrane 40 and thus the interior of the membrane 40 is in fluid communication with the interior of the ceramic substrate 32 and the lumen of the elongated plastic tubular member 12. The membrane preferably comprises a biaxially oriented polyethylene terathalate (PET) material but polyvinyl chloride or polyethylene can be used as well.

With reference to FIG. 4, in use, the catheter with the tip member 28 on its distal end is snaked through the vascular system until the exposed electrodes $E_1$ and $E_2$ are juxtaposed relative to the stenotic lesion to be ablated. Once this is done, an inflation fluid may be injected through the proximal inflation port 19 which then flows through the lumen of the tube 12, the hollow interior of the ceramic member 32 and through the ports 38 to inflate the expander Doing so causes the electrodes to be brought into contact with a predetermined area of the stenotic lesion. Now, when RF energy is applied from the generator (not shown) and across the terminal pins 20 and 22, the conductors 24 and 26 cause that potential to be impressed across the spaced electrodes $E_1$ and $E_2$. The spacing of the electrodes is such that at the RF voltage employed, an arc discharge will result to excise the material comprising the stenotic lesion. By rotating the catheter body, the electrodes can be brought into contact with the entire surface of the lesion.

Figures 6, 7:
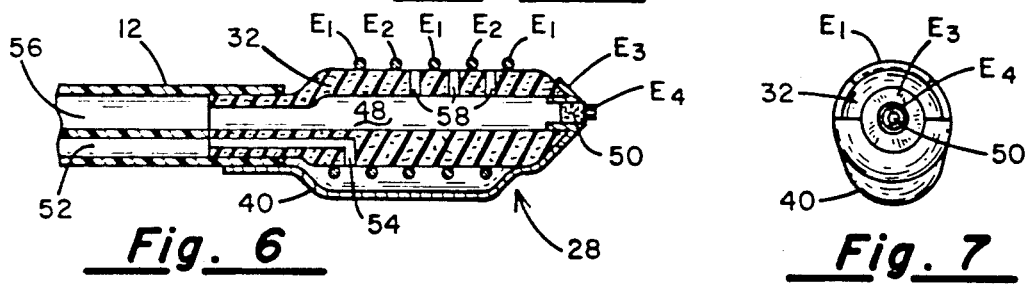
FIG. 6 is a cross-sectional view of a tip member in accordance with FIG. 2 but including a second electrode set.
FIG. 7 is a right end view of the embodiment of FIG. 6.

Referring next to FIGS. 6 and 7 there is shown an alternative embodiment of the tip member for an ablation catheter to be used in situations where the plaque in a particular blood vessel substantially occludes the vessel to the extent that the tip member cannot be passed through the blood vessel to the extent shown in FIGS. 4 and 5. The tip member of the embodiment of FIGS. 6 and 7 includes a further pair of bipolar electrodes labeled $E_3$ and $E_4$ and located on the distal end surface of the tip member 28. Electrode $E_3$ is formed from an appropriate metal and is generally annular in shape and has a stem portion fitting within a longitudinal bore 48 formed through the ceramic core portion 32. A ceramic plug 50 is dimensioned to fit within the distal end of the bore 48 and carried on the external side surface of the plug 50 is a ring-shaped electrode $E_4$. As can best be seen in the end view of FIG. 7, a gap, typically approximately 0.005 inches exists between the electrodes $E_3$ and $E_4$ such that they are normally insulated from one another.

To avoid confusion in the view of FIG. 6, the wire or ribbon conductors used to couple the RF voltage generator at the proximal end of the catheter to the electrode pairs $E_1$-$E_2$ and $E_3$-$E_4$ are not depicted. In a typical fashion, they Would be made to traverse the lumen of the catheter body 12 or, alternatively, may be embedded in the wall of the tube 12 and then the distal end portion of these elongated conductors are appropriately joined to the four electrodes.

As with the embodiment of FIGS. 2 through 4, an inflatable expander member 40 is bonded to the Teflon ® layer 34 which covers the helical windings on which the electrodes $E_1$ and $E_2$ are exposed and generally encompasses the lower half of the tip member when viewed as in FIG. 6. The tubular body member 12 in the embodiment of FIG. 6 includes an inflation lumen 52 which joins to a bore 54 formed in the ceramic body 32. By injecting a fluid, such as saline solution, into the inflation lumen 52, it perfuses therealong and through the bore 54 to fill the expander member 40 to a pressure sufficient to inflate it and effectively increase the cross-sectional profile of the tip member to the point where the electrode surfaces $E_1$ and $E_2$ are brought into engagement with the plaque deposit to be ablated. Now, when an appropriate RF potential is developed across the electrodes $E_1$ and $E_2$, an arc is created which is effective to cut through the athero-stenotic lesion. By simultaneously rotating the catheter, the tip member, and especially the electrodes $E_1$ and $E_2$ disposed on a defined surface thereof, can be made to wipe across the lesion occupying an internal circumference of a blood vessel.

As previously mentioned, if the lumen through the lesion is so constricted that the tip member 28 cannot be forced therethrough, a tunnel-like opening can be created by connecting RF energy across the distal electrodes $E_3$ and $E_4$ to again create an arc discharge as the distal end is pushed up against the lesion.

The tip member 28 shown in FIG. 6 also includes means for either flushing or aspirating at the wound site. When flushing, a saline solution may be injected through the flush lumen 56 from the proximal end of the catheter and thence through the bore 48 and out the transverse ports 58. Alternatively, by coupling a source of vacuum to the proximal end of the catheter so as to communicate with the lumen 56, a previously injected flushing liquid mixed with blood, and possibly particles of the lesion being ablated, can be drawn through the ports 58, the longitudinal bore 48 and the lumen 56.

Figure 8:
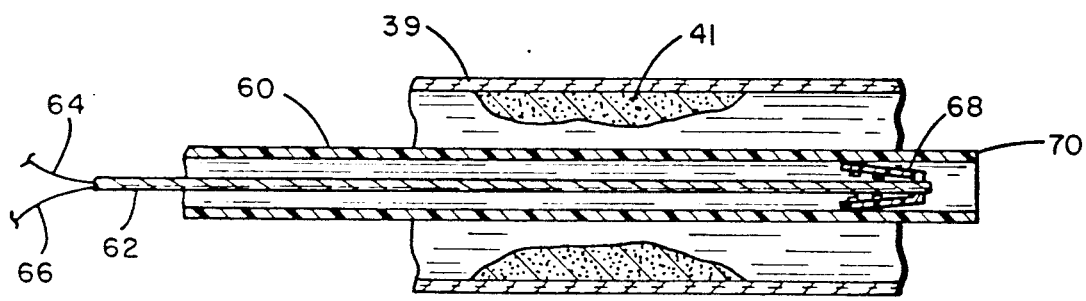
FIG. 8 is a side cross-sectional view of another embodiment of the invention with he tip member in its low profile state.
Figure 9:
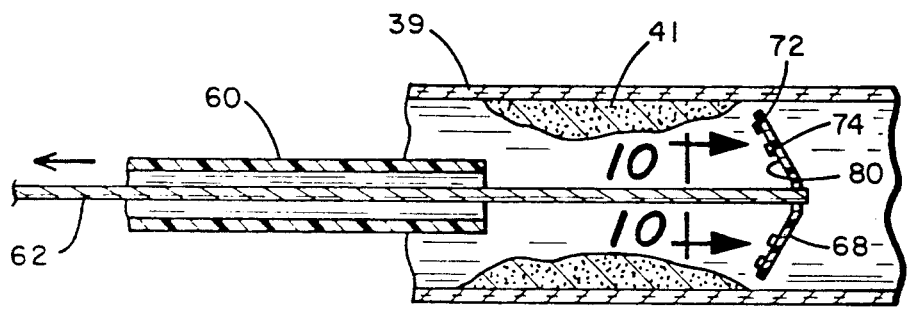
FIG. 9 is a side cross-sectional view of the embodiment of FIG. 8 but with the tip member in its expanded state.
Figure 10:
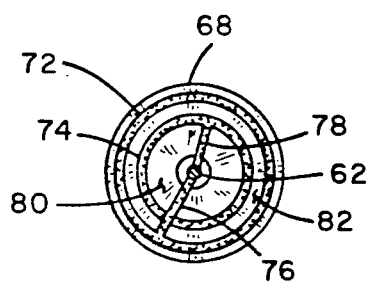
FIG. 10 is a cross-sectional view taken along the line 10—10 in FIG. 9.

Referring next to FIGS. 8-10, a further embodiment of the ablation catheter with means for deploying electrodes following the positioning of the distal end of the ablation catheter at the treatment site is shown. In this arrangement, an elongated flexible plastic tubular member 60 of a predetermined diameter has fitted within the lumen thereof an inner flexible tube 62 through which a pair of elongated, insulated flexible conductors 64 and 66 extend. The tube 60 may typically be a guide catheter. As will be later described, conductors 64 and 66 join to spaced-apart electrodes affixed to a radially expandable carrier 68 which in FIG. 8 is shown in its collapsed form within the lumen of the tube 60. As shown in that Figure, the catheter 60 is first routed through the vascular system until its distal end 70 has passed beyond the site of the stenotic lesion 41 to be removed. Next, and as illustrated in FIG. 9, when the catheter body 60 is retracted in the proximal direction while holding the inner tubular member 62 stationary, the carrier member 68 is freed from the confines of the lumen of the tube 60 and is free to expand.

With reference to FIG. 10, it can be seen that there is formed on the proximal side of the carrier 68 a pair of annular electrodes 72 and 74 which are connected by radial traces 76 and 78 to the conductors 64 and 66 extending through the inner tube 62. The carrier member 68 is preferably formed from a material exhibiting a memory property and capable of operating at the temperatures encountered during the RF ablation process. For example, but without limitation, the carrier 68 may be formed from a thin wafer of phosphor bronze alloy whose surface 80 is coated with a layer of insulation, for example, a ceramic. Then, deposited on the insulating layer are the spaced annular electrodes 72 and 74. Moreover, a suitable masking technique can be used to create the conductor patterns on the surface 80, such processes being well known in the hybrid circuitry field.

When the carrier member 68 is popped free of the lumen of the tube 60, it opens like an umbrella and presents the electrodes 72 and 74 to the distal side of the lesion 41. Now, by retracting the inner tubular member 62, the electrodes 72 and 74 are made to engage the plaque deposit. With a suitably high RF current provided, an arc is created across the gap 82 separating the conductors 72 and 74 from one another. This arc is effective to excise the lesion as it is pulled in the proximal direction through the lesion. At the same time, a vacuum may be applied to the proximal end of the catheter 60 to draw blood and any entrained debris created during the RF ablation out of the blood vessel.

Figure 11:
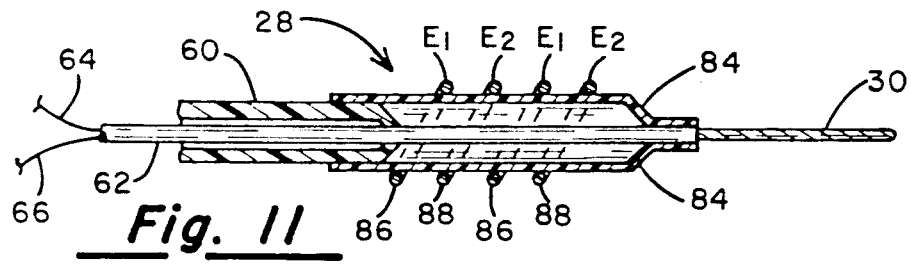
FIG. 11 is a cross-sectional view of yet another embodiment of the invention showing the electrodes in their low profile state.
Figure 12:
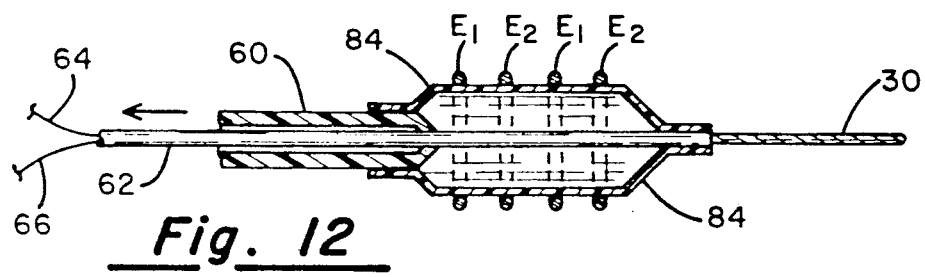
FIG. 12 is a cross-sectional view of the embodiment of FIG. 11 with the electrodes shown in their extended state.

FIGS. 11 and 12 depict yet another embodiment of an RF ablation catheter in which the distal tip member is at a relatively low cross-sectional profile during the initial placement of the catheter in the vascular system with the tip member at the treatment site, yet allowing the tip member to be expanded to a relatively larger profile at the time the RF cutting is to take place. This arrangement is seen to include an outer tubular member 60 and inner tubular member 62 which freely passes through the lumen of the tube 60. The tube 62 extends beyond the distal end of the tube 60 and bonded to the distal end portion of each of the tubes 60 and 62 are a series of flexible strips as at 84. Typically, four such strips are used and are spaced at 90° intervals around the cylindrical body of the catheter assembly.

First and second helical wires 86 and 88 wound around the strips in non-contacting relationship creating a predetermined size gap therebetween. The conductors 86 and 88 are preferably coated with an insulation over the majority of the surface thereof, but as in the embodiment of FIG. 2 an electrode area is created by grinding away the insulation over a predetermined segment of those conductors. A fixed guidewire 30 may again be connected to the distal end of the tip member to facilitate routing the catheter through the vascular system to the desired treatment location.

Upon reaching the treatment site and juxtaposing the tip member 28 with the lesion to be excised, the physician may pull back on the inner tube 62 while holding the outer tube 60 fixed. This results in the straps 84 bowing radially outwardly as shown in FIG. 12, causing the turns 86 and 88 to assume a more vertical disposition. This increases the cross-sectional profile of the tip member. This maneuver is intended to cause the electrodes $E_1$ and $E_2$ to engage the lesion to be treated. Then, RF current is fed through the conductors 64 and 66 leading to the tip electrodes. The energy supplied may be sufficient to create an electric arc between adjacent electrode pairs. This arc or electrical transmission, being close to or in contact with the tissue of the lesion, causes an electrosurgical cutting action or an electrical searing or fixation effect to take place. That is, by applying lesser energy, a sustained arc may not result, but sufficient heating can be produced to alter the cells comprising the lining of the vessel and to sear the tissue structures Again, a source of negative pressure may be coupled to the proximal end of the catheter so that blood and possibly other debris may be aspirated through the lumen of the tubular catheter 60.

Figure 13:
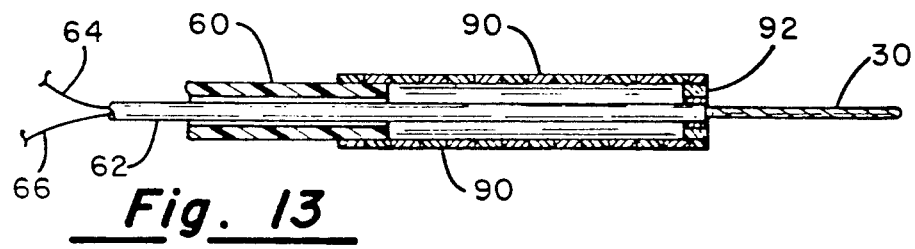
FIG. 13 is a cross-sectional view of yet another embodiment of the invention with the electrodes shown in their low profile state.
Figure 14:
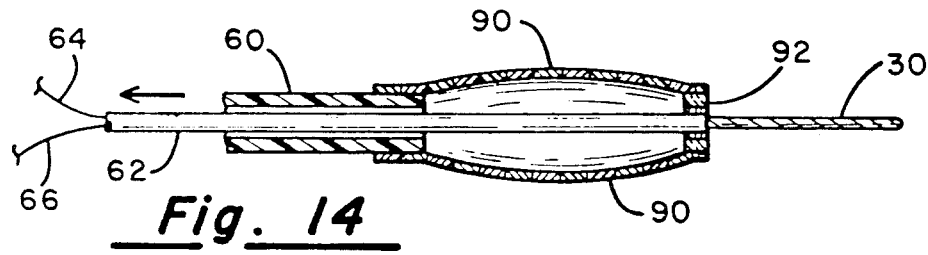
FIG. 14 is a cross-sectional view of the embodiment of FIG. 13 with the electrodes shown in their extended state.

The embodiment shown in FIGS. 13 and 14 is somewhat closely related to that shown in FIGS. 11 and 12. However, in the later instance, the tip member comprises a plurality of closely-spaced, thin, flexible, conductive strips 90 which are attached at their proximal end to the distal end of the outer tubular member 60. The distal end of the strips 90 are joined to a generally circular insulating disk 92 to which the distal end of the inner tubular member 62 connects. The wires 64 and 66 extend through the lumen of the inner tubular member 62 and respectively join to alternate conductive strips 90 forming a bipolar electrode pair.

The ablation catheter, and especially its distal tip member, is then routed through the vascular system with the tip member in its low profile state as shown in FIG. 13. Upon being juxtaposed relative to the lesion to be excised, the physician retracts the inner tubular member 62, again creating a bowing action of the flexible conductive strip 90 as illustrated in FIG. 14. This brings the bipolar electrodes 90 into engagement with the stenotic lesion to be removed.

Figure 15:
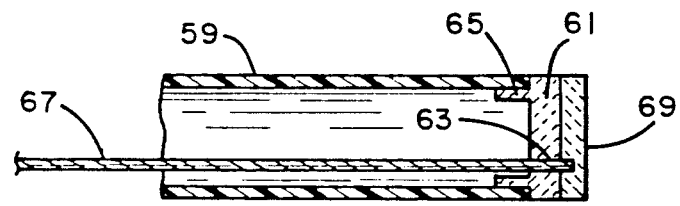
FIG. 15 is a cross-sectional view of a yet further embodiment of the invention with the electrodes in their low profile orientation.
Figure 16:
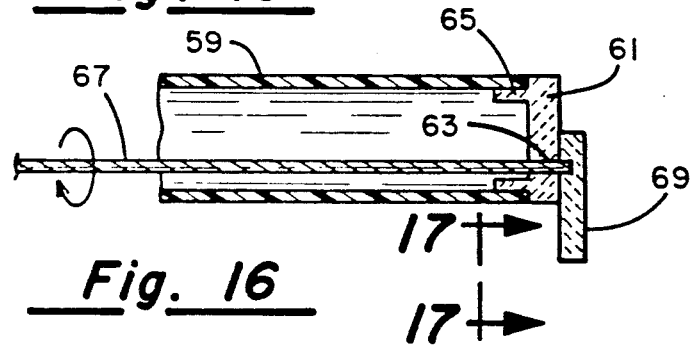
FIG. 16 is a cross-sectional view of the embodiment of FIG. 15 with the electrodes being deployed in their extended state.
Figure 17:
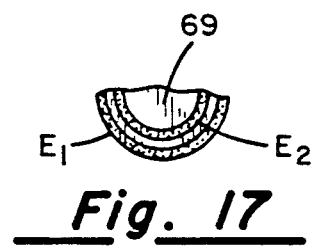
FIG. 17 is a view taken along lines 17—17 in FIG. 16.

FIGS. 15 through 17 illustrate yet another embodiment of the present invention. Here, an outer tubular member 59 has fitted into its distal end a circular ceramic plug 61 having a longitudinal bore 63 extending therethrough. The plug 61 is bonded to the outer tube 59 along a circumferential seam 65 and thus remains stationary relative to the tube 59. Passing through the bore 63 are a pair of conductors 67. They are insulated from one another but wound together in such a fashion that a torque applied to the proximal end of the wound conductors 67, i.e., at the proximal end of the elongated tubular catheter 59, will be transmitted to rotate a circular disk 69 to which the twisted conductors 67 are joined. The disk 69 is illustrated as being in its rotated disposition in the cross-sectional view of FIG. 16. FIG. 17 illustrates the pattern of metallization comprising the bipolar electrodes which are formed on the proximal surface of the disk 69. Again, two generally circular arcs spaced from one another by a predetermined gap create a bipolar electrode pair $E_1$ and $E_2$.

As those skilled in the art will appreciate from the description of the prior embodiments, in the case of the present embodiment, in use, the catheter 59 of FIG. 16 will be routed through the vascular system to the treatment site and somewhat distal thereof. During this phase, the disk 69 is generally concentric with the catheter body 59. Once ablation is to be performed, the physician will rotate the coiled wires 67 and, in doing so, will also rotate the disk 69 in the fashion illustrated in FIG. 16. With an appropriate RF voltage applied across the electrodes $E_1$ and $E_2$, an arc condition can be created and when the catheter is pulled rearward, i.e., in its proximal direction, the electrodes $E_1$ and $E_2$ formed on the disk 68 will engage the lesion and cut through it. It is also contemplated that a torque applying member other than the coiled wires 67 may be used to rotate the disc carrying the electrodes.

The pieces 61 and 69 are preferably fabricated from ceramic such as silicon nitride or aluminum nitride and the electrodes $E_1$ and $E_2$ are plated, screened or otherwise formed on the surface of the disk 69 in any of a number of available and well-known processes.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An RF ablation catheter for electrosurgically removing tissue deposits form the interior walls of a blood vessel, comprising:
   (a) a first elongated, flexible, plastic, tubular member having a distal end, a proximal end, a lumen extending therebetween and an outside diameter which is less than the diameter of the lumen of the blood vessel to be treated;
   (b) a second elongated, flexible, tubular member longitudinally movable within the lumen of said first tubular member and having a proximal end, a distal end and a lumen extending therebetween;
   (c) an umbrella-shaped flexible carrier member affixed to the distal end of said second tubular member, said carrier member being formed from an insulating material and having first and second electrode patterns formed on a given surface of said carrier member, said carrier member constrained to fit within said lumen of said first tubular member and being self-expandable to a predetermined larger diameter than that of said lumen of said first tubular member when said distal end of said second tubular member is moved longitudinally to the point where said distal end of said second tubular member is advanced beyond said distal end of said first tubular member to thereby expose said electrode patterns relative to said tissue deposits to be removed; and
   (d) conductor means extending through said lumen of said second tubular member from said proximal end and to said distal end of said second tubular member and electrically connected to said first and second electrode patterns for applying an RF voltage across said electrode patterns.

2. The RF ablation catheter as in claim 1 wherein said first and second electrode patterns generally comprise concentric circles of conductive materials which are electrically insulated from one another.

3. The RF ablation catheter as in claim 2 wherein said given surface is a proximal facing surface of said carrier member.

4. The RF ablation catheter as in claim 1 wherein said carrier member is formed from a material exhibiting a memory property.

5. The RF ablation catheter as in claim 1 wherein said carrier member comprises:
   (a) a relatively thin wafer of phosphor bronze alloy; and
   (b) an insulation layer formed on said wafer, said electrode patterns being disposed on said layer of insulation.

* * * * *